US00PP30123P3

(12) United States Plant Patent
Goffreda et al.

(10) Patent No.: US PP30,123 P3
(45) Date of Patent: Jan. 22, 2019

(54) NECTARINE TREE NAMED 'NJN103'

(50) Latin Name: ***Prunus persica* var. *nucipersica***
Varietal Denomination: NJN103

(71) Applicant: RUTGERS, THE STATE UNIVERSITY OF NEW JERSEY, New Brunswick, NJ (US)

(72) Inventors: Joseph C. Goffreda, Millstone Township, NJ (US); Anna M. Voordeckers, East Windsor Township, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 4 days.

(21) Appl. No.: 15/530,547

(22) Filed: Jan. 26, 2017

(65) Prior Publication Data

US 2018/0213692 P1 Jul. 26, 2018

(51) Int. Cl.
*A01H 5/08* (2018.01)
*A01H 6/74* (2018.01)

(52) U.S. Cl.
USPC ..... Plt./188
CPC ..... *A01H 6/7454* (2018.05)

(58) Field of Classification Search
USPC ..... Plt./188, 189
CPC ..... A01H 5/0856; A01H 5/08; A01H 5/00; A01H 5/0881; A01H 6/7454; A01H 6/7481
See application file for complete search history.

(56) References Cited

PUBLICATIONS

Callahan Michigan Show Peach and Plum Great Lakes Expo, Plums, Pluots, Flat Peach, and Other Novel Stone Fruits Nov. 22, 2016, retrieved on Mar. 5, 2018, retrieved from the Internet at www.glexpo.com/summaries/2016summaries/Peach-Plum.pdf, 13 pp. (Year: 2016).*

* cited by examiner

*Primary Examiner* — June Hwu
(74) *Attorney, Agent, or Firm* — Patrick J. Daugherty; Daugherty & Del Zoppo Co., LPA

(57) ABSTRACT

A new and distinct nectarine variety of *Prunus persica* named 'NJN103' is provided. This variety is distinguished from other nectarine varieties by its unique combination of showy flowers, glossy semi-freestone fruit, with an attractive red over color, ripening in early-midseason, with white juicy flesh, and sweet, moderately acidic flavor that is maintained following cold storage.

6 Drawing Sheets

Latin name of genus and species of the plant claimed: *Prunus persica* var. *nucipersica.*
Variety denomination: NJN103.

CROSS REFERENCE TO RELATED APPLICATIONS

NONE

STATEMENT REGARDING FEDERALLY SPONSORED RESEARCH OR DEVELOPMENT

NONE

BACKGROUND OF THE INVENTION

The present invention relates to a new and distinct variety of nectarine tree named 'NJN103'. Our new tree resulted from crossing 'Fantasia' (non-patented) nectarine as the seed parent with 'NJN100' (U.S. Plant Pat. No. 18,147) nectarine tree as the pollen parent. The new variety differs from seed parent 'Fantasia' in that the new variety has white flesh instead of yellow, and ripens about four weeks earlier. The new variety differs from pollen parent 'NJN100' in that the new variety produces larger fruit that ripen about 10 days later. The resulting tree was selected when growing in a cultivated area as the $42^{nd}$ tree in the $54^{th}$ row of Block K at a fruit research farm in Cream Ridge, N.J.

BRIEF SUMMARY OF THE INVENTION

The 'NJN103' variety is distinguished from other nectarine varieties due to the following unique combination of characteristics: nearly round to broad elliptic fruit with a low tendency to split when adequately cropped; large, glossy fruit with an attractive red over color that have white flesh; good production of firm fruit that ripen in early-midseason; fruit with a good to very good eating quality that are sweet and moderately acidic. In comparison to the 'Arctic Glo' variety (described by expired U.S. Plant Pat. No. 7,884) 'NJN103' produces larger fruit, with a more balanced, sweet-tart flavor.

The variety was asexually reproduced at the fruit research farm in Cream Ridge, N.J. Asexual reproduction of this new variety by budding onto 'Lovell' peach seedling rootstock (non-patented) shows that the foregoing characteristics are so reproduced.

The following detailed description concerns the original tree, 'NJN103'. The original tree and asexual progeny have been observed growing in a cultivated area at the fruit research farm in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to *The Royal Horticultural Society* (*R.H.S.*) *Colour Chart* (1966).

BRIEF DESCRIPTION OF THE DRAWINGS

This new variety is illustrated by the accompanying photographic drawings, depicting the nectarine tree at the approximate age of six (6) years old by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
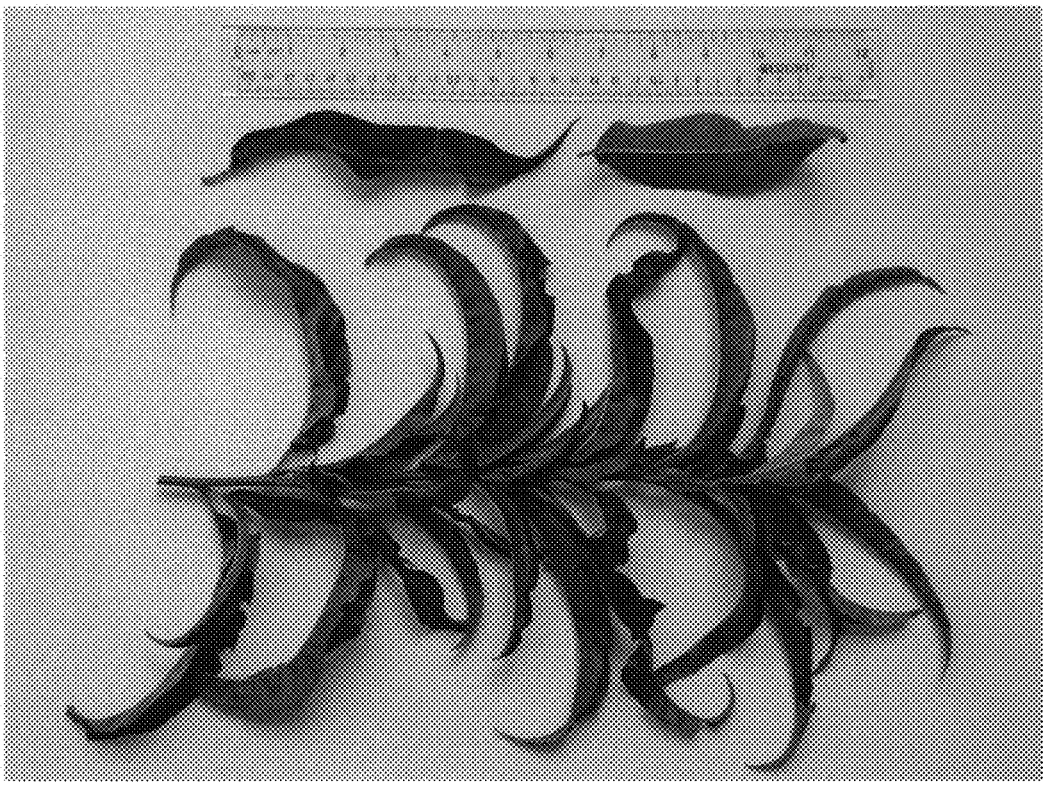
FIG. 1 is a color photograph taken on Aug. 16, 2013 of a characteristic twig of 'NJN103' in late spring bearing typical leaves of the foliage.
Figure 2:
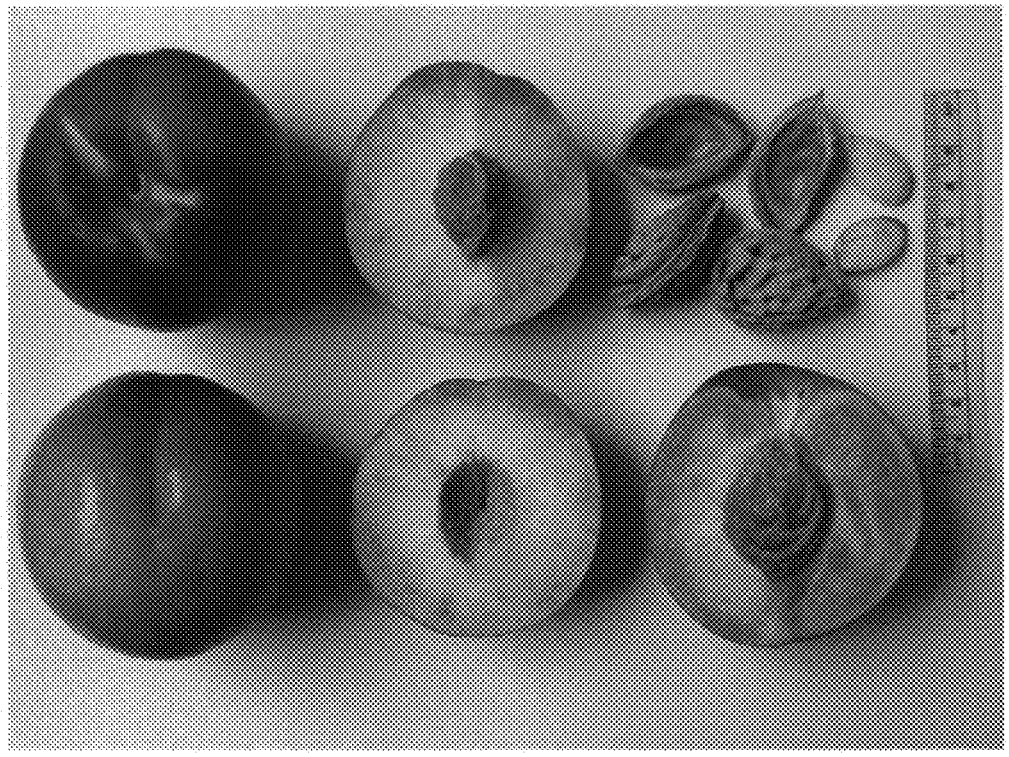
FIG. 2 is a color photograph taken on Aug. 8, 2013 of characteristic mature fruit and stones of 'NJN103'. Whole fruit are presented in three positions and both a transverse and longitudinal cross section to illustrate that the pericarp does not adhere to the pit when the fruit is mature. The stones exemplify the obovate shape and pits and grooves on the surface of the stone. Two kernels are depicted removed from the stones, next to a view of one stone split in half that depicts smooth inner surfaces from which one of the kernels is removed.
Figure 3:
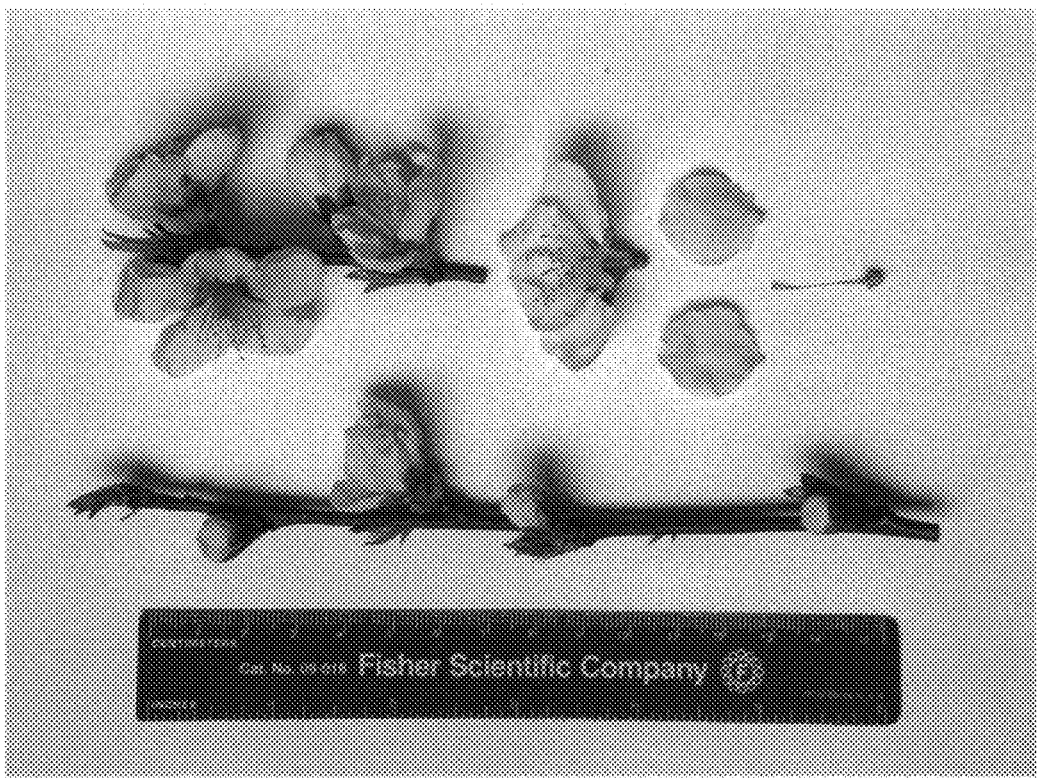
FIG. 3 is a color photograph of a characteristic twig that illustrates the typical flower buds and large, showy flowers of 'NJN103' observed on a tree at said fruit research farm in Cream Ridge, N.J. on Apr. 23, 2014. The single organ depicted in FIG. 3 is the pistil.
Figure 4:
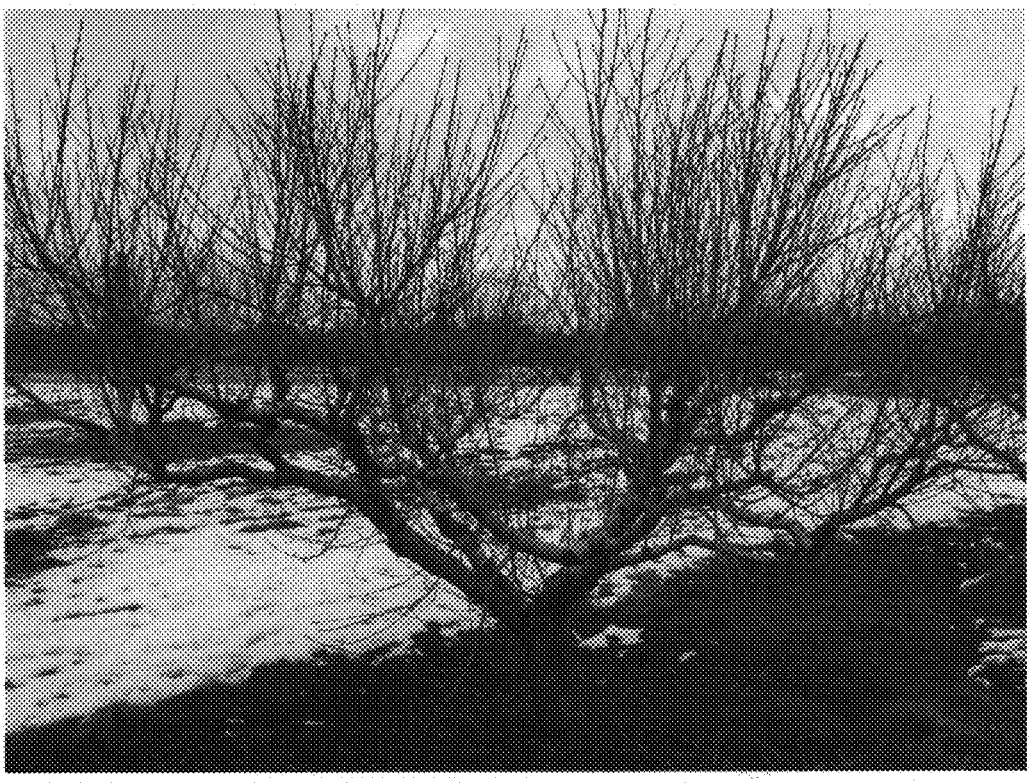
FIG. 4 is a color photograph of a dormant tree of 'NJN103', prior to pruning, in late winter that illustrates the spreading growth habit of a tree at the fruit research farm in Cream Ridge, N.J. on Feb. 8, 2016.
Figure 5:
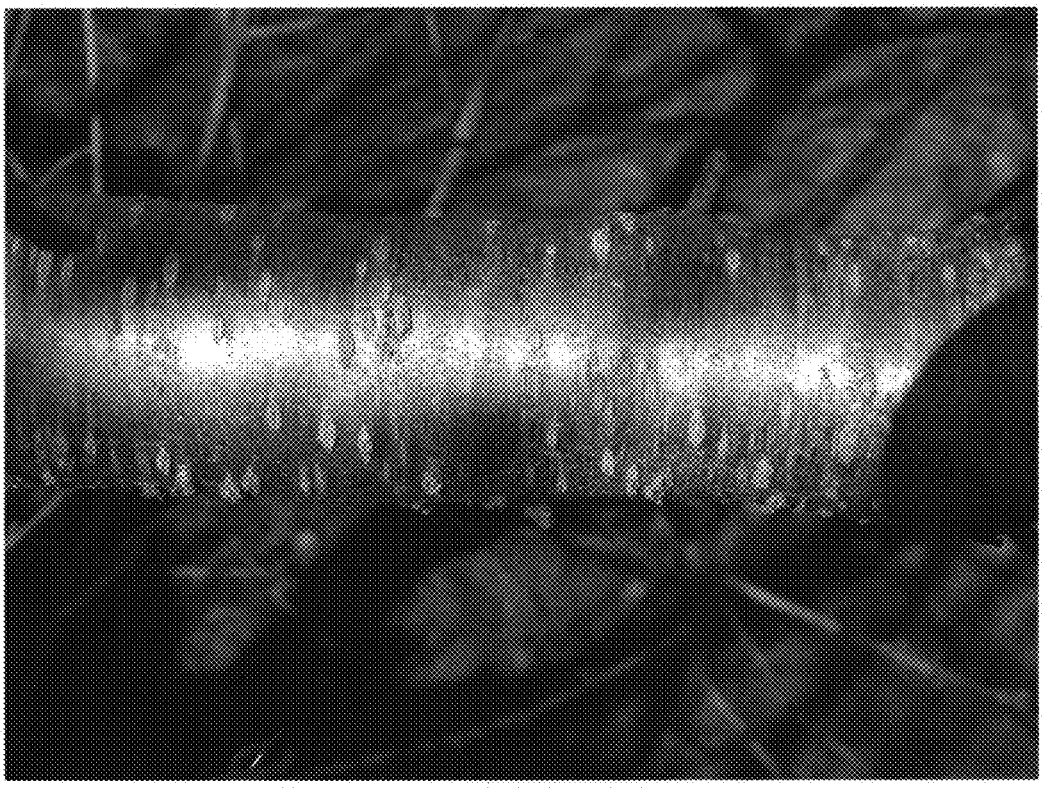
FIG. 5 is a color photograph taken on Mar. 17, 2015 of immature bark of 'NJN103' that illustrates color and the moderate density of conspicuous elliptic lenticels on the immature bark.
Figure 6:
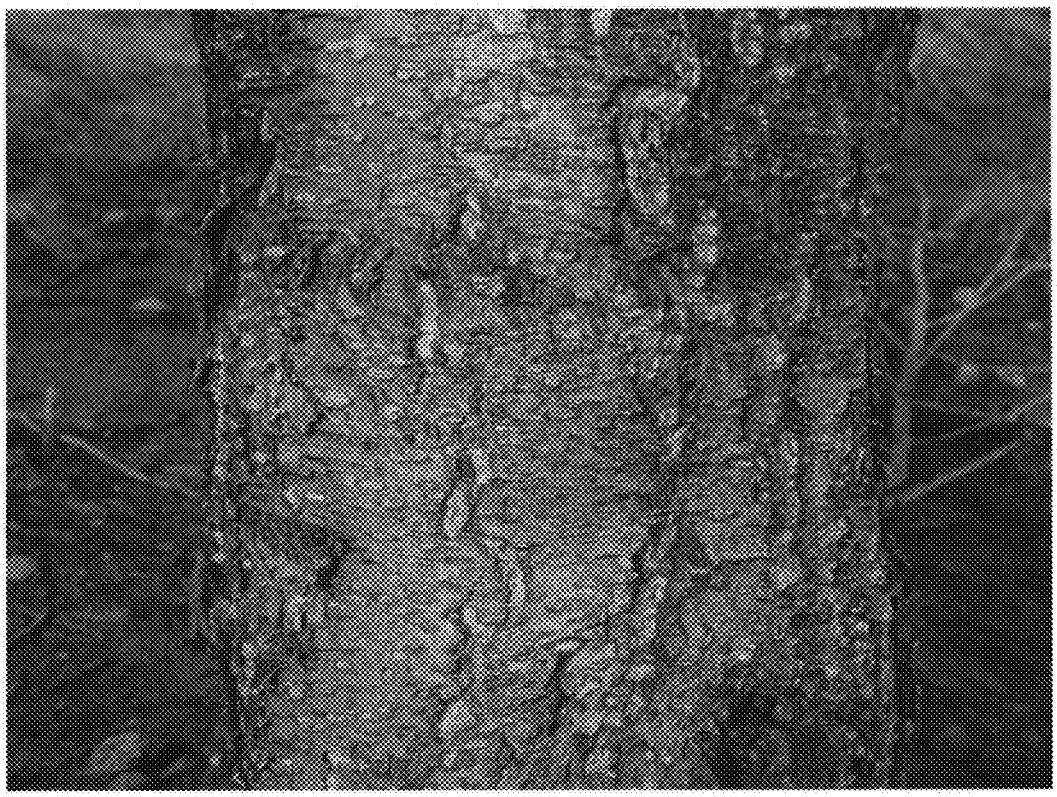
FIG. 6 is a color photograph taken on Mar. 11, 2015 of mature bark of 'NJN103' that illustrates greyed-green color and rough texture with many shallow furrows of the mature bark.

The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'NJN103' variety is based on observations of an asexually reproduced tree. The observed tree was six years of age and growing on 'Lovell' seedling rootstock (non-patented) at the fruit research farm in Cream Ridge, N.J.

Scientific name: *Prunus persica* var. *nucipersica*.

Parentage:

*Seed parent*.—'Fantasia'.

*Pollen parent*.—'NJN100'.

Tree:

*Vigor*.—Vigorous.

*Plant hardiness zone*.—Growth of plants has only been observed in zone 6b.

*Dormant flower bud cold tolerance*.—At least to −20° C.

*Overall shape*.—Spreading.

*Height*.—Average as compared to other nectarine cultivars. For example, measurement of a typical grafted tree on 'Lovell' peach seedling rootstock (non-patented) at six years after planting shows an average height of 3.4 meters when grown in Cream Ridge, N.J.

*Width*.—Average as compared to other nectarine cultivars. For example, measurement of a typical grafted tree on 'Lovell' peach seedling rootstock (non-patented) at six years after planting shows an average width of 4.6 meters when grown in Cream Ridge, N.J.

*Caliper*.—Six year old tree is 59 cm in circumference measured at 20 cm from the ground.

Trunk and branches:

*Trunk bark texture*.—Rough with many shallow furrows.

*Trunk bark color*.—Greyed-green (between RHS 197C and RHS 197D).

*Primary branches*.—Branches that are approximately 16 cm in circumference are greyed-green (between RHS 198C and RHS 198D).

*Lenticels*.—Moderate density, approximately 1.0 per square cm; elliptical in shape and conspicuous; typical examples of which averaged 5.3 mm in length and 2.7 mm in width; greyed-green (RHS 198D) in color becoming greyed-orange (RHS 173C) towards the center.

*Branch pubescence*.—None.

*New growth bark*.—Greyed-purple (RHS 183A) in sun; color yellow-green (RHS 152D) in shade.

*Internodes*.—Length averaging 25.8 mm on a one-year shoot.

Leaves:

*Texture*.—Glabrous, both surfaces.

*Sheen*.—Young leaves semi-glossy with a flat finish on the underside.

*Length*.—About 166 mm to 198 mm, averaging about 186 mm including the petiole.

*Width*.—About 37 mm to 42 mm, averaging about 40 mm.

*Petiole*.—Averaging 11.68 mm long and about 2.0 mm in diameter.

*Margin*.—Crenate.

*Margin undulation*.—Moderate.

*Form*.—Lanceolate, and concave in cross section.

*Apex*.—Sharply acuminate, curved downward.

*Base*.—Cuneate.

*Venation*.—Pinnate.

*Glands*.—Number: About 2 to 4, averaging about 2.8. Position: Generally, located on the leaf margin near its base and petiole. Size: Length averaging 1.5 mm and width averaging 1.0 mm. Form: Reniform.

*Stipules*.—None observed on mature leaves. Stipules are present on immature leaves, but they are not persistent; typically, there are two per immature leaf, with an average length of 8.4 mm, wherein the color is yellow-green (RHS 146 B).

*Leaf color*.—Upper leaf surface: Green (between RHS 137B and RHS 137C). Lower leaf surface: Yellow-green (between RHS 147B and RHS 147C). Vein: Yellow-green (RHS 145D).

*Pubescence*.—None.

*Leaf bud burst*.—In 2014, generally from April 16 through April 24.

Flowers:

*Size*.—Large size, typical flower measuring between 30 mm to 50 mm, averaging about 40 mm across.

*Color*.—Dormant bud: Grey (RHS 201D) becoming Grey (RHS 201A) near the base. Pink stage bud: Red-purple (between RHS 62A and RHS 62B). Open flower: Red (RHS 56C).

*Petals*.—Typically five petals per flower; cupped, nearly round, with moderate undulation at the margin, averaging about 21.1 mm long and 19.3 mm wide.

*Petal apex*.—Obtuse, nearly rounded.

*Petal base*.—Cuneate.

*Stamens*.—Position: perigynous and near or slightly below the point of attachment of the petals. The stigma is approximately at the same level of anthers on the longest stamens. Number: Variable, typical range 35 and 43, averaging 38.4. Length: Variable, between 8 mm to 14 mm, averaging 11.5 mm. Filament color: White (RHS 155D). Anther color: Adaxial surface is greyed-red (RHS 180B); abaxial surface is (RHS 161B) greyed-yellow.

*Pistil*.—Number: One. Size: Length between 18 and 22 mm, averaging 20.4 mm. Pistil color: Yellow-green (RHS 145B). Ovary: Glabrous and ellipsoid in shape, color yellow-green (RHS 145A).

*Sepals*.—Number: Five. Pubescence: Length short, fine, low density becoming denser near the margin. Color: Greyed-red (RHS 182A) becoming greyed-green (RHS 197B) near the margin. Shape: Triangular, with a rounded apex. Size: Length averaging 6.8 mm, width averaging 4.5 mm.

*Hypanthium*.—Also known as the "nectar cup" or "floral cup", color of surface between the point of attachment of the petal/stamens and the ovary of the flower is greyed-orange (RHS 163B).

*Pollen*.—Abundant; yellow (RHS 11A) in color.

*Fragrance*.—Very slight.

*Bloom season*.—Onset of bloom in 2014 on April 16; full bloom on April 24.

Fruit:

*Size*.—Large, averaging about 7.2 cm long, 6.7 cm wide parallel to the suture and 6.7 cm wide perpendicular to the suture.

*Typical weight*.—172 g.

*Form*.—Longitudinal section: Nearly round. Traverse section: Nearly round to broad elliptic.

*Stalk cavity*.—Averages about 3.2 mm deep and 4.1 mm wide.

*Suture*.—Shallow.

*Ventral surface*.—Nearly smooth.

*Base*.—Flat.

*Apex*.—Round; apex tip is a small, point.

*Stem*.—Average length of 9.3 mm and an average diameter of 3.7 mm.

*Skin*.—Thickness: Medium. Surface: Glabrous, typically glossy. Tenacity: Medium. Astringency: None. Tendency to crack: Low. Color: Two distinct red blush colors were observed on the fruit: Red (RHS 38A) was found on the portion(s) of the skin in the shade, whereas red (RHS 53A) was found on the portions(s) of the skin in full sun; ground color yellow-orange (RHS 18D).

*Fruit properties*.—Flesh color: White (RHS 155C) mottled with red (RHS 42A) near the skin and the stone. Flesh adhesion: Semi-freestone, sometimes becoming freestone when fully mature. Flesh firmness: Good, comparable to other known commercial nectarine varieties. Juice: Moderate. Texture: Melting. Fibers: Not noticeable. Ripens: Between July 21 and July 31 at Cream Ridge, N.J. Flavor: Typically sweet and moderately acidic. Soluble solids: 11.6%. Aroma: Moderate. Eating quality: Good to very good.

*Keeping quality*.—Medium. Has held its flavor and firmness for at least 14 days in cold storage at 1° C. to 2° C.

*Shipping quality*.—Good. No bruising or scaring disorders have been observed.

*Usage*.—Dessert.

*Market*.—Local and long distance.

*Productivity*.—Moderate. Trees have produced a full crop in 6 out of 10 years, and at least a partial crop in 8 out of 10 years at Cream Ridge, N.J.

Stone:

*Type*.—Semi-freestone sometimes becoming freestone when soft ripe.

*Form*.—Obovate.

*Base*.—Medium.

*Apex*.—Narrow.

*Surface*.—Pits and grooves.

*Ventral suture*.—Small to medium, truncated at apex.

*Dorsal ridge*.—Low to medium height, broad width, forming deep lines.

*External color*.—Greyed-orange (between RHS 165C and RHS 165D).

*Cavity surface color*.—Greyed-orange (RHS 165D).

*Average stone dry weight*.—6.3 g.

*Average stone wall thickness*.—Varies between 5.2 mm along the dorsal ridge to 9.5 mm at the base.

*Size*.—Averages about 39.5 mm long, 24.6 mm wide parallel to the dorsal ridge, and 19.9 mm wide perpendicular to the dorsal ridge.

*Tendency to split*.—Typically low when well cropped.

Kernel:

*Form*.—Elliptic to slightly obovate.

*Skin color*.—Greyed-orange (RHS 165B).

*Vein color*.—Greyed-orange (RHS 165C).

*Viability*.—Yes, but may need to be germinated in tissue culture.

*Size*.—Averages about 19.2 mm long, 11.8 mm wide, and 1.8 mm in breadth.

Plant/fruit disease and pest resistance/susceptibility: No atypical resistances/susceptibilities have been noted under normal cultural practices.

We claim:

1. A new and distinct variety of nectarine tree, substantially as herein shown and described.

* * * * *